United States Patent [19]
Slater

[11] Patent Number: 6,019,758
[45] Date of Patent: *Feb. 1, 2000

[54] ENDOSCOPIC BIPOLAR MULTIPLE SAMPLE BIOPTOME

[75] Inventor: Charles R. Slater, Ft. Lauderdale, Fla.

[73] Assignee: Symbiosis Corporation, Miami, Fla.

[*] Notice: This patent is subject to a terminal disclaimer.

[21] Appl. No.: 08/946,883

[22] Filed: Oct. 8, 1997

Related U.S. Application Data

[63] Continuation of application No. 08/584,801, Jan. 11, 1996, Pat. No. 5,683,388.

[51] Int. Cl.⁷ ................................................. A61B 17/39
[52] U.S. Cl. .............................. 606/51; 606/41; 606/205; 600/566
[58] Field of Search ........................... 606/41, 42, 45–52, 606/205–208; 600/562, 564, 566

[56] References Cited

U.S. PATENT DOCUMENTS

| | | |
|---|---|---|
| 3,920,021 | 11/1975 | Hiltebrandt . |
| 4,985,030 | 1/1991 | Melzer et al. . |
| 5,147,357 | 9/1992 | Rose et al. . |
| 5,324,289 | 6/1994 | Eggers . |
| 5,445,638 | 8/1995 | Rydell et al. ............................. 606/51 |
| 5,458,598 | 10/1995 | Feinberg et al. ......................... 606/52 |
| 5,482,054 | 1/1996 | Slater et al. . |
| 5,542,432 | 8/1996 | Slater et al. . |
| 5,697,949 | 12/1997 | Giurtino et al. ......................... 606/205 |
| 5,849,022 | 12/1998 | Sakashita et al. ....................... 606/174 |

FOREIGN PATENT DOCUMENTS

| | | |
|---|---|---|
| 623316 | 11/1994 | European Pat. Off. . |
| 9417741 | 8/1994 | WIPO . |

*Primary Examiner*—Michael Peffley
*Attorney, Agent, or Firm*—Finnegan, Henderson, Farabow, Garrett & Dunner, LLP

[57] ABSTRACT

An endoscopic bipolar multiple sample bioptome includes a relatively long conductive flexible member having a lumen with an axially displaceable conductive wire extending therethrough and covered with an electrically insulating sheath. The proximal ends of the flexible member and wire are coupled to a manual actuation device for axially displacing one of the flexible member and wire relative to the other and the manual actuation device is provided with bipolar electrical couplings for electrically coupling one pole of a current source to the flexible member and the other pole of the current source to the wire. The distal end of the flexible member is mechanically and electrically coupled to a partially conductive cylinder having a distal edge and the distal end of the wire is mechanically and electrically coupled to the jaw assembly. The jaw assembly includes a pair of opposed toothed jaw cups each of which is coupled by a narrow resilient arm to a base member. The base member is mounted inside the cylinder and axial movement of the base member relative to the cylinder draws the necks of the jaws into the cylinder to bring the jaw cups together in a biting action. The cylinder is substantially non-conductive with portions of its exterior being conductive. Cautery current flows between the jaw assembly and the conductive portion(s) of the cylinder by way of tissue which is being cauterized.

28 Claims, 4 Drawing Sheets

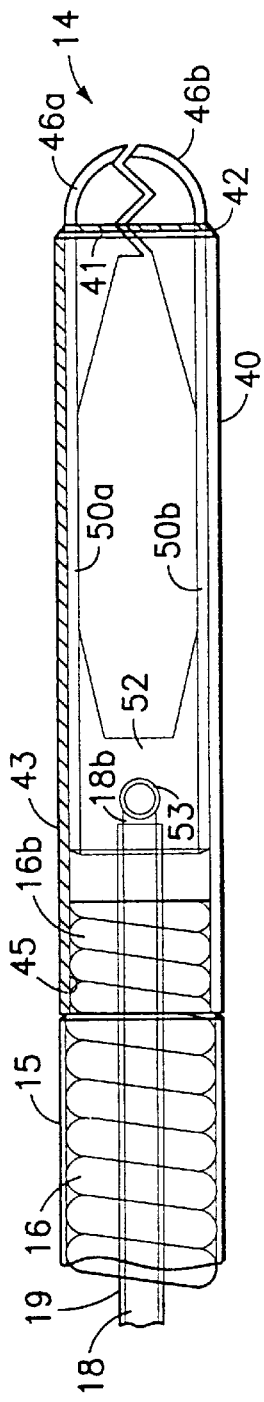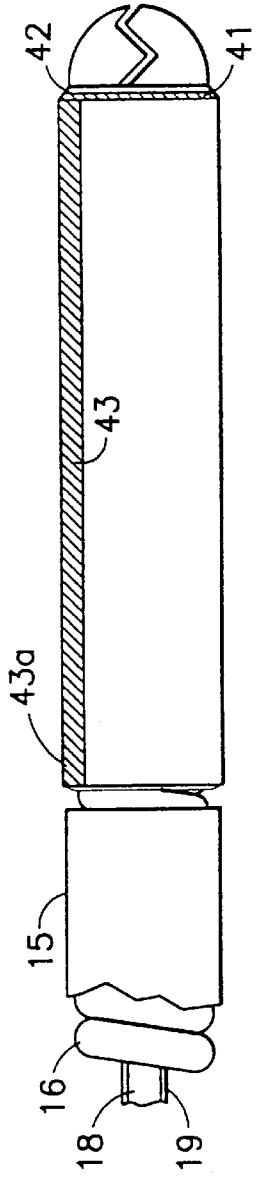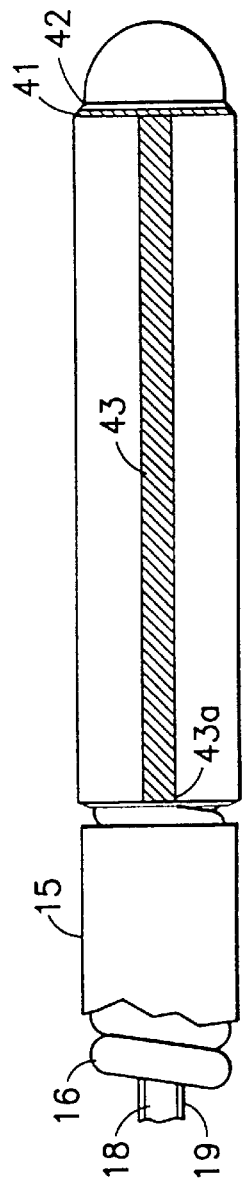

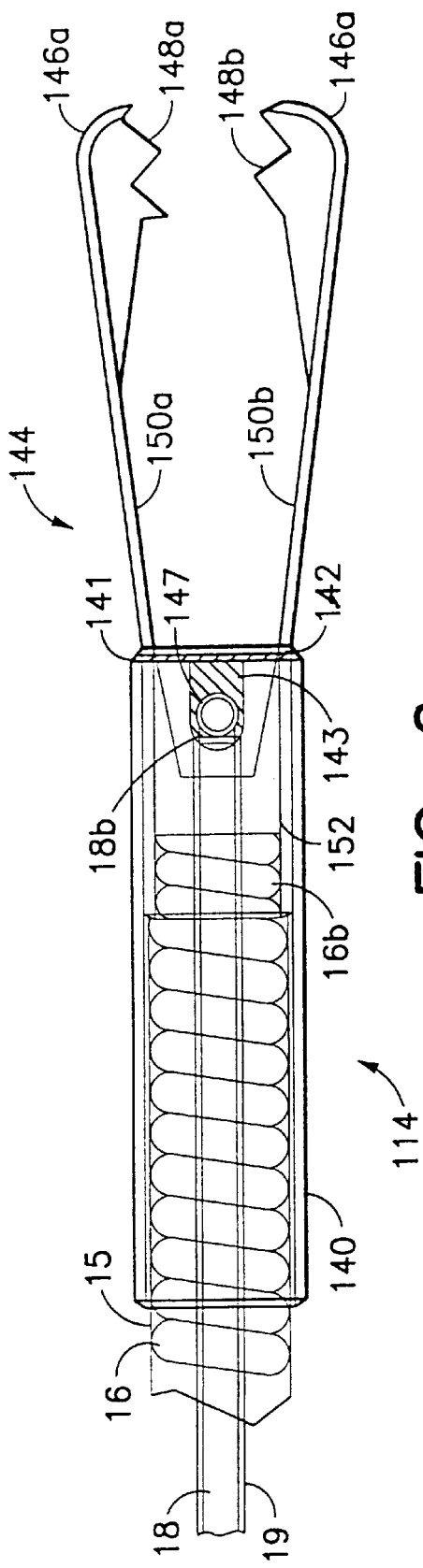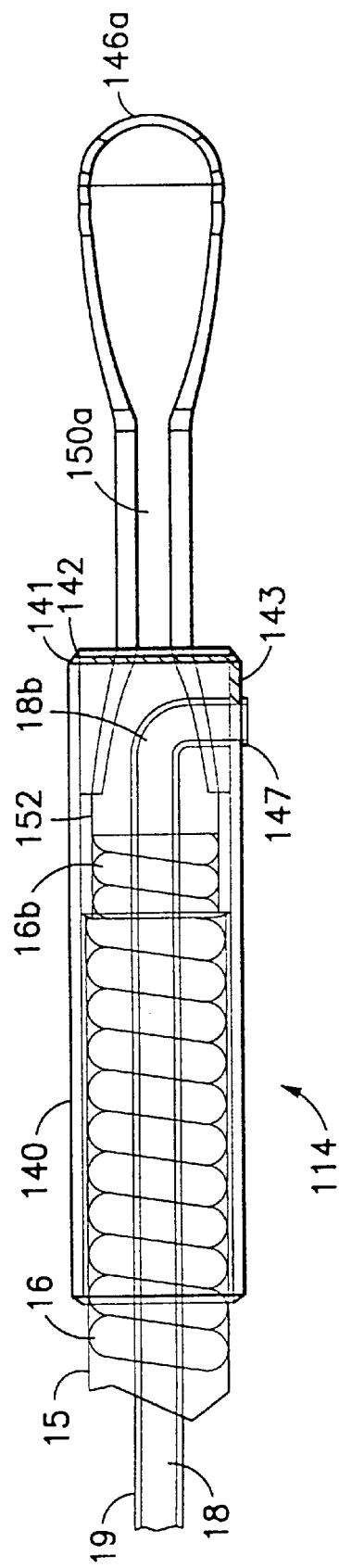
FIG. 6
FIG. 7

ENDOSCOPIC BIPOLAR MULTIPLE SAMPLE BIOPTOME

This is a continuation of application Ser. No. 08/584,801, filed Jan. 11, 1996, now U.S. Pat. No. 5,683,388.

This application is related to co-owned applications Ser. No. 08/189,937 filed Feb. 1, 1994, now U.S. Pat. No. 5,542,432, Ser. No. 08/265,217 filed Jun. 24, 1994, now U.S. Pat. No. 5,482,054, Ser. Nos. 08/440,326 and 08/440,327 both filed May 12, 1995, now U.S. Pat. Nos. 5,638,827 and 5,645,075 respectively, all of which are hereby incorporated by reference herein in their entirety.

BACKGROUND OF THE INVENTION

1. Field of the Invention

This invention relates to endoscopic surgical instruments. More particularly, this invention relates to an instrument for taking multiple biopsy tissue samples and which is provided with bipolar cautery capability.

2. State of the Art

Endoscopic biopsy procedures are typically performed with an endoscope and an endoscopic biopsy forceps device (bioptome). The endoscope is a long flexible tube carrying fiber optics and having a narrow lumen through which the bioptome is inserted. The bioptome typically includes a long flexible coil having a pair of opposed jaws at the distal end and manual actuation means at the proximal end. Manipulation of the actuation means opens and closes the jaws. During a biopsy tissue sampling operation, the surgeon guides the endoscope to the biopsy site while viewing the biopsy site through the fiber optics of the endoscope. The bioptome is inserted through the narrow lumen of the endoscope until the opposed jaws arrive at the biopsy site. While viewing the biopsy site through the fiber optics of the endoscope, the surgeon positions the jaws around a tissue to be sampled and manipulates the actuation means so that the jaws close around the tissue. A sample of the tissue is then cut and/or torn away from the biopsy site while it is trapped between the jaws of the bioptome. Keeping the jaws closed, the surgeon withdraws the bioptome from the endoscope and then opens the jaws to collect the biopsy tissue sample.

A biopsy tissue sampling procedure often requires the taking of several tissue samples either from the same or from different biopsy sites. Unfortunately, most bioptomes are limited to taking a single tissue sample, after which the device must be withdrawn from the endoscope and the tissue collected before the device can be used again to take a second tissue sample. The single-sample limitation of most bioptomes is due to the limited space between the biopsy forceps jaws. Several attempts have been made to provide an instrument which will allow the taking of several tissue samples before the instrument must be withdrawn and the samples collected. Problems in providing such an instrument include the extremely small size required by the narrow lumen of the endoscope and the fact that the instrument must be flexible in order to be inserted through the lumen of the endoscope.

Co-owned application Ser. No. 08/189,937 discloses an endoscopic multiple sample bioptome which includes a relatively long flexible member having a lumen with an axially displaceable wire extending therethrough. The proximal ends of the flexible member and wire are coupled to a manual actuation means for axially displacing one of the flexible member and wire relative to the other. The distal end of the flexible member is coupled to either a cylinder preferably having a knife sharp distal edge, or a jaw assembly. The distal end of the wire is coupled to the other of the cylinder and the jaw assembly. The jaw assembly includes a pair of opposed toothed jaw cups each of which is coupled by a narrow arm to a base member. The narrow arm of each jaw is preferably formed from Nitinol as described in U.S. Ser. Nos. 08/440,326 and 08/440,327 and is arranged to urge the jaws away from each other. The base member of the jaw assembly is mounted inside the cylinder and axial movement of one of the jaw assembly and cylinder relative to the other draws the necks of the jaws into the cylinder or moves the cylinder over the necks of the jaws to bring the jaw cups together in a biting action.

Clearly, where traumatic procedures such as taking a biopsy are being conducted, the ability to conduct endoscopic cautery procedures is desirable in order to stem bleeding. While both monopolar and bipolar endoscopic cautery instruments are known (such as disclosed in U.S. Pat. No. 4,418,692 to Guay), increasingly, bipolar cautery is preferred because it is less traumatic to the patient. In bipolar cautery instruments, the electric current path is from one electrode, through the tissue to be cauterized, and then through to the other electrode and out of the instrument. Thus, cauterization is limited to only that tissue between the two electrodes. On the other hand, in monopolar instruments, the patient effectively becomes the second electrode, and the cautery current is dissipated through the patient. In the monopolar situation, control of the cautery location is not exact, and tissue surrounding the tissue to be cauterized is also subject to different degrees of cautery.

In U.S. Pat. No. 4,763,660 to Jaeger, a bipolar endoscopic microelectrocautery device is shown. The Jaeger patent also discloses a device for obtaining biopsies. However, the device disclosed in Jaeger requires a number of different single function "instrument heads" only one of which may be attached at any time to the instrument for performing a specific function such as grasping, cutting, or cauterizing. Thus, the biopsy forceps "head", is incapable of cauterizing, while the cauterizing "head" is incapable of obtaining a biopsy. This arrangement does not permit the surgeon to cauterize at the biopsy site at the time of taking a biopsy.

SUMMARY OF THE INVENTION

It is therefore an object of the invention to provide an endoscopic multiple sample bioptome which has bipolar cautery capability.

It is also an object of the invention to provide an endoscopic bipolar multiple sample bioptome which has all of the advantages of traditional biopsy forceps with the added abilities to collect multiple samples and to apply bipolar cautery.

In accord with these objects which will be discussed in detail below, the endoscopic bipolar multiple sample bioptome of the present invention includes a relatively long conductive flexible member having a lumen with an axially displaceable conductive wire extending therethrough which is covered with an electrically insulating sheath. The proximal ends of the flexible member and wire are coupled to a manual actuation means for axially displacing one of the flexible member and wire relative to the other and the manual actuation means is provided with bipolar electrical coupling means for electrically coupling one pole of a current source to the flexible member and the other pole of the current source to the wire. The distal end of the flexible member is mechanically and electrically coupled to one of a partially conductive cylinder having a distal edge and a conductive jaw assembly. The distal end of the wire is mechanically and electrically coupled to the other of the cylinder and the jaw assembly. The jaw assembly includes a pair of opposed jaw cups each of which is coupled by a narrow arm to a base member. The narrow arm of each jaw is a resilient member which urges each jaw away from the other. The base member of the jaw assembly is mounted inside the cylinder and axial movement of one of the jaw assembly and cylinder relative to the other draws the necks of the jaws into the cylinder or moves the cylinder over the necks of the jaws to bring the jaw cups together in a biting action. The partially conductive cylinder has a substantially non-conductive interior and portions of its exterior surface are conductive. When a source of cautery current is coupled to the bipolar couplings in the manual actuation means, cautery current flows between the jaw assembly and the conductive portion(s) of the cylinder. Since the interior of the cylinder is non-conductive, there is no short circuit caused by the interior of the cylinder embracing the necks of the jaw assembly.

Preferred aspects of the invention include: forming the flexible member as a coil; coupling the cylinder to the distal end of the coil; forming the jaw assembly from Nitinol; providing teeth on the jaw cups; coupling the jaw assembly to the axially displaceable wire; and providing both the wire and the coil with respective insulating sheaths along substantially their entire lengths. According to one embodiment of the invention, the cylinder is formed from a ceramic material and plated with electrically conductive traces which extend from its coupling with the coil to its distal edge. According to another embodiment, the cylinder is formed from anodized aluminum. A portion of the outer surface of the cylinder is masked before the cylinder is anodized to render the unmasked portions non-conductive.

Additional objects and advantages of the invention will become apparent to those skilled in the art upon reference to the detailed description taken in conjunction with the provided figures.

BRIEF DESCRIPTION OF THE DRAWINGS

FIG. 3 is an enlarged transparent side elevation view of the distal end of the bioptome of FIGS. 1 and 2 with the jaws closed;

FIG. 4 is an enlarged side elevation view of the distal end of the bioptome of FIGS. 1–3 with the jaws closed;

FIG. 5 is an enlarged top view of the distal end of the bioptome of FIGS. 1–4 with the jaws closed;

FIG. 6 is an enlarged transparent side elevation view of the distal end of a second embodiment of a bipolar multiple sample bioptome according to the invention with the jaws in an open position;

FIG. 7 is an enlarged transparent top view of the distal end of the bioptome of FIG. 6.

DETAILED DESCRIPTION OF THE PREFERRED EMBODIMENTS

Figure 1:
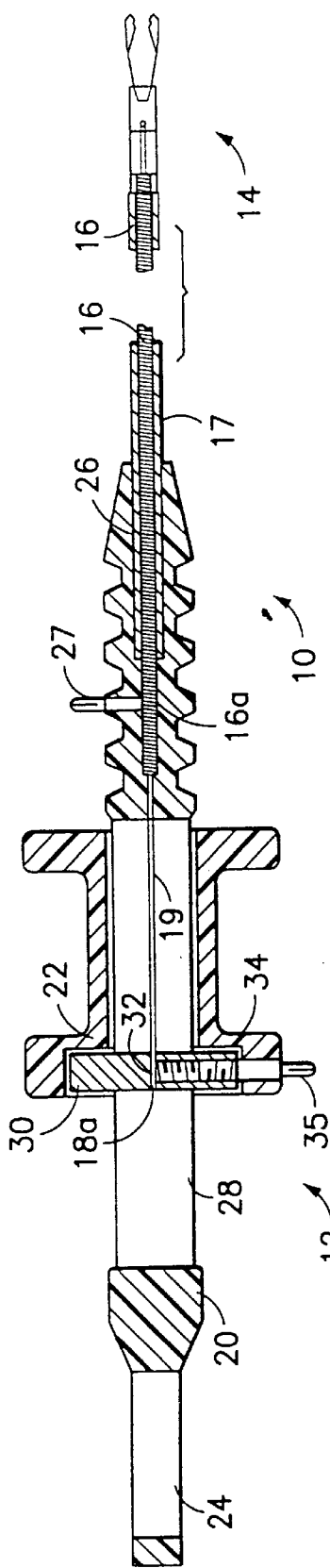
FIG. 1 is a broken, transparent side elevation view in partial section of a first embodiment of a bipolar multiple sample bioptome according to the invention.

Referring now to FIGS. 1 through 5, the bipolar multiple sample bioptome 10 includes a proximal handle 12 and a distal end effector 14. A long flexible electrically conductive coil 16 having an axially displaceable control wire 18 extending therethrough couples the handle 12 and the end effector 14. The coil 16 is preferably covered with a non-conductive PTFE, FEP or polyethylene sheath 15 along substantially all of its length except for its proximal end 16a and its distal end 16b. A strain relief sleeve 17 preferably covers a portion of the coil 16 which extends from the handle 12. The control wire 18 is preferably covered with an electrically non-conductive sheath 19 substantially all of its length except for its proximal end 18a and its distal end 18b. The proximal handle 12 includes a central shaft 20 and a displaceable spool 22. The proximal end of the shaft 20 is provided with a thumb ring 24 and a longitudinal bore 26 is provided at the distal end of the shaft 20. A longitudinal slot 28 extends from the proximal end of bore 26 to a point distal of the thumb ring 24. The proximal end 16a of the coil 16 is mounted in the bore 26 and a radially engaging electrical connector 27 contacts the uninsulated end 16a of the coil 16. The displaceable spool 22 is provided with a cross member 30 which passes through the slot 28 in the central shaft 20. The cross member 30 is provided with a central through hole 32 and a radially engaging set screw 34 having an electrical connector 35. The uninsulated proximal end 18a of the control wire 18 is engaged by the set screw 34. From the foregoing, those skilled in the art will appreciate that relative movement of the shaft 20 and spool 22 results in movement of the control wire 18 relative to the coil 16. Such action results in actuation of the end effector 14 as described in detail below.

Turning now to FIGS. 2 through 5, the end effector 14 includes a partially conductive cylindrical sleeve 40 having a (preferably sharp) distal edge 42, and a conductive jaw assembly 44. The jaw assembly 44 includes a pair of opposed jaw cups 46a, 46b each preferably having a plurality of sharp teeth 48a, 48b. A resilient, preferably narrow, arm 50a, 50b extends proximally from each jaw cup 46a, 46b. A cylindrical base member 52 joins the proximal ends of the arms 50a, 50b. The narrow resilient arms 50a, 50b are biased apart from each other, thereby urging the jaw cups 46a, 46b apart. According to a preferred embodiment of the invention, the cylindrical base member 52 of the jaw assembly 44 is mechanically and electrically coupled to the uninsulated distal end 18b of the control wire 18 by providing the base member 52 with a lateral hole 53 and providing the distal end 18b of the control wire with a substantially right angle bend. The distal end 18b of the control wire 18 is soldered or otherwise electrically and mechanically attached in the hole 53 in the base member 52. The cylindrical sleeve 40 is coupled to the uninsulated distal end 16b of the coil 16 by crimping and/or soldering. According to this embodiment of the invention, the partially conductive sleeve 40 has a first conductive area in the form of a ring 41 near the distal edge 42 and a second conductive area in the form of a longitudinal stripe 43 which extends from the ring 41 to the proximal end of the sleeve 40. The proximal end 43a of the stripe 43 is electrically coupled to the distal end 16b of the coil 16, preferably by soldering. Optionally, a third conductive area 45 is provided on the proximal edge and interior of the proximal end of the sleeve 40 and makes electrical contact with the distal end 16b of the coil 16. It will be appreciated that the conductive ring 41 is therefore electrically coupled to the coil 16 via the stripe 43, and optionally the third conductive area 45.

Figure 2:
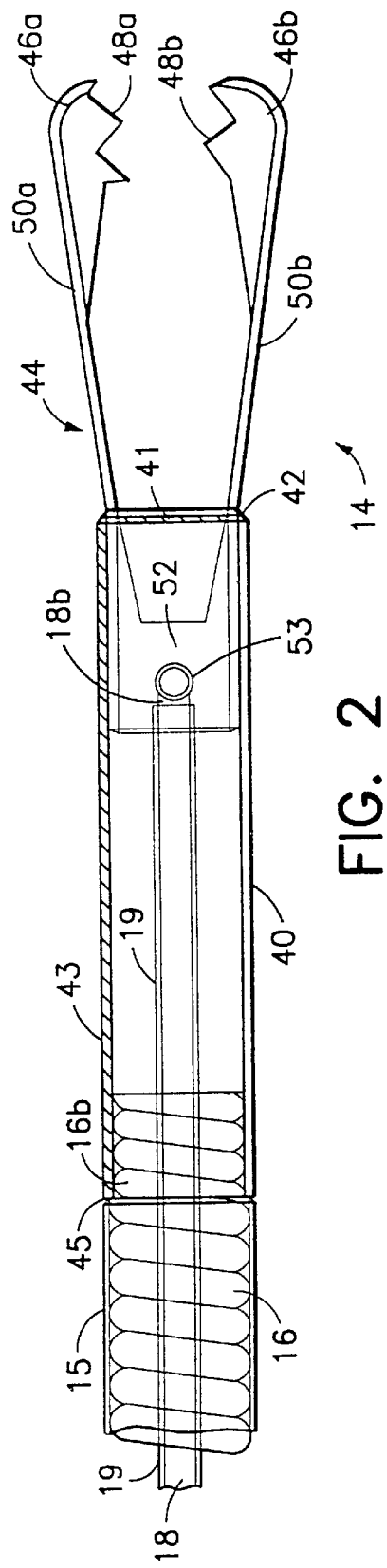
FIG. 2 is an enlarged transparent side elevation view of the distal end of the bioptome of FIG. 1 with the jaws open.

From the foregoing description those skilled in the art will appreciate that when the spool 22 and the shaft 20 are axially displaced relative to each other, the cylindrical sleeve 40 and the jaw assembly 44 are similarly axially displaced relative to each other, from the positions shown in FIG. 2 to the positions shown in FIG. 3 and vice versa. It will also be appreciated that when the spool 22 and shaft 20 are in the approximate position shown in FIG. 1, the cylindrical sleeve 40 and the jaw assembly 44 will be in the approximate position shown in FIG. 2; i.e., with the jaws open. Thus, those skilled in the art will further appreciate that when the spool 22 is moved towards the thumb ring 24, or vice versa, the cylindrical sleeve 40 and the jaw assembly 44 will be brought into the approximate position shown in FIG. 3 by movement of the jaws into the sleeve, thereby closing the jaws.

It will also be understood that one pole of a bipolar cautery source (not shown) which is coupled to the electrical connector 27 will be electrically coupled to the ring 41 on the sleeve 40 via the coil 16 and another pole of the bipolar cautery source which is coupled to the electrical connector 35 will be electrically coupled to the jaws 46a, 46b via the control wire 18. Since the jaw assembly 44 never comes in contact with the conductive portions 41, 43, 45 of the sleeve 40 (ring 41 being separated from the jaws by the non-conductive distal edge 42) and since the control wire 18 is insulated from the coil 16 by the sheath 19, short circuits are avoided during all phases of the biopsy procedure. When cautery current is supplied to the end effector assembly 14, if tissue is present at the edge 42, current passes between the conductive ring 41 and the arms 50a, 50b or the jaws 46a, 46b via the tissue (not shown) depending on the position of the jaw assembly 44 relative to the sleeve 40.

According to one embodiment of the invention, the sleeve 40 is made of a non-conductive ceramic material and the conductive areas 41, 43, and optionally 45 are applied by tracing with a conductive material. For example, the conductive material may be applied by vapor deposition, thermal spray, or other means of metalization onto a ceramic sleeve where the sleeve is first masked to cover areas which will remain non-conductive.

According to another embodiment of the invention, sleeve 40 is made of aluminum which is then anodized. Prior to anodizing the sleeve, portions of the sleeve are masked so that they will remain conductive after the unmasked portions of the sleeve are anodized.

Figure 8:
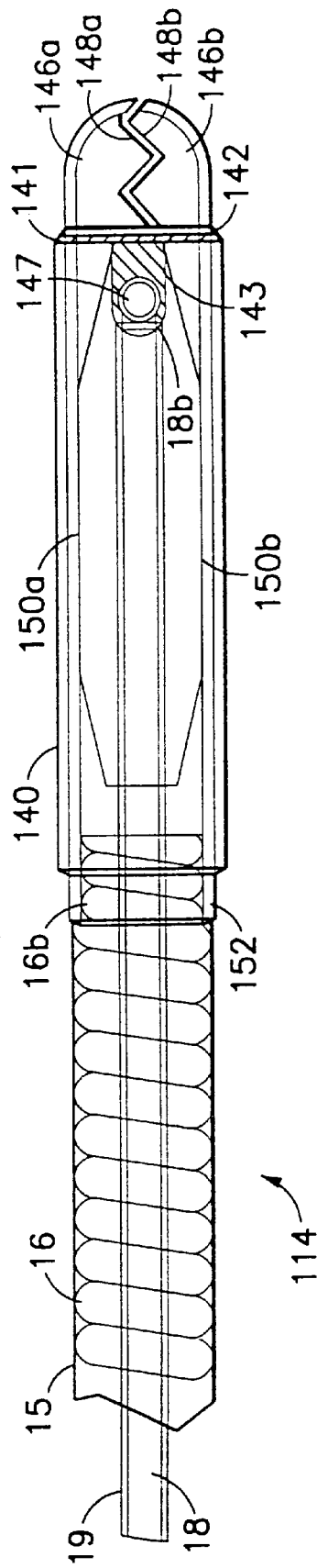
FIG. 8 is an enlarged transparent side elevation view of the distal end the bioptome of FIGS. 6 and 7 with the jaws in a closed position.

Turning now to FIGS. 6–8, according to a second embodiment of the invention, an end effector assembly 114 is coupled to the distal ends of the coil 16 and control wire 18. The end effector assembly 114 is similar to the end effector assembly 14 described above in that it includes a cylindrical sleeve 140 and a jaw assembly 144. The jaw assembly 144 is substantially the same as the jaw assembly 44 described above, with similar reference numerals indicating similar parts. In this embodiment, however, the cylindrical base 152 of the jaw assembly 144 is mechanically and electrically coupled to the distal end 16b of the coil 16 by crimping and/or soldering. The cylindrical sheath 140 is also similar to the cylindrical sheath 40 described above having a (preferably sharp) distal edge 142, a conductive ring 141 near the distal edge 142, and a conductive stripe or portion 143 which extends proximally from the conductive ring 141. In this embodiment, however, the sleeve 140 is electrically and mechanically coupled to the distal end 18b of the control wire 18. The coupling is effected by providing a lateral hole 147 in the sleeve 140 and a right angle bend in the distal end 18b of the control wire 18. The end of the control wire is inserted in the hole and is soldered or otherwise mechanically and electrically connected to the sleeve. As seen in FIGS. 6–8 the conductive portions 141 and 143 of the sleeve 140 make electrical contact with the distal end of the control wire 18 via the hole 147.

It should be appreciated that when the endoscopic instrument with the jaw assembly 114 is actuated, the sheath 140 will be moved by the control wire 18 over the arms 150a, 150b and jaw cups 146a, 146b. Because the arms are narrow, there is sufficient room for the right angled bend in the insulated wire 18 to extend between the arms and out to the sheath 140 without contact being made between the wire and the arms. In addition, if desired, the connection between the control wire and the sheath can be made more proximally along the sheath to avoid contact between the control wire and biopsy samples collected between the arms.

There have been described and illustrated herein several embodiments of an endoscopic bipolar multiple sample bioptome. While particular embodiments of the invention have been described, it is not intended that the invention be limited thereto, as it is intended that the invention be as broad in scope as the art will allow and that the specification be read likewise. Thus, while particular configurations of the handle have been disclosed, it will be appreciated that other types of handles could be utilized. Also, while specific couplings of the ends of the coil and control wire have been shown, it will be recognized that other types of couplings could be used with similar results obtained. Moreover, while particular configurations have been disclosed in reference to the jaw assembly, it will be appreciated that other configurations could be used as well. For example, while it is preferred to provide jaws with teeth, it will be appreciated that in lieu of teeth, the jaws can be provided with sharp edges which, in conjunction with a sharp cylindrical sleeve, will provide a cutting ability. Furthermore, while the jaw assembly has been disclosed as being formed from Nitinol, it will be understood that different formations of the jaw assembly can achieve the same or similar function as disclosed herein. Further yet, it will be appreciated that while the apparatus of the invention was described as advantageously permitting the obtaining of multiple biopsies without removal from the surgical site, the apparatus of the invention, if desired, could still be used for obtaining single biopsies at a time. With regard to the partially conductive sleeve, it will be appreciated that the arrangement of the conductive portions may be varied considerably so long as the conductive portions of the sleeve do not contact the jaw assembly. It will therefore be appreciated by those skilled in the art that yet other modifications could be made to the provided invention without deviating from its spirit and scope as so claimed.

We claim:

1. A bipolar bioptome comprising:

a proximal handle assembly including an actuator;

a distal end effector assembly including electrically conductive end effectors and an electrically conductive distal member proximate to and electrically isolated from the end effectors, the distal member being movable relative to the end effectors;

a connection member mechanically coupling the actuator to the end effector assembly, the connection member having first and second electrically conductive portions, wherein actuation of the actuator causes the distal member to move relative to the end effectors and thereby open and close the end effectors; and an electrical coupling for supplying one pole of a current source through the first conductive portion to the distal member and the other pole of the current source through the second conductive portion to the end effectors so that current flows between the distal member and the end effectors during a biopsy procedure.

2. The bipolar bioptome of claim 1, wherein the first conductive portion includes a hollow, electrically conductive coil electrically coupled to the distal member.

3. The bipolar bioptome of claim 2, further comprising a non-conductive sheath over at least a portion of the coil.

4. The bipolar bioptome of claim 1, wherein the first and second conductive portions are electrically isolated from each other.

5. The bipolar bioptome of claim 1, wherein the second conductive portion includes an electrically conductive control wire electrically coupled to the end effectors.

6. The bipolar bioptome of claim 5, further comprising a non-conductive sheath over at least a portion of the control wire.

7. The bipolar bioptome of claim 1, wherein the second conductive portion includes a hollow, electrically conductive coil electrically coupled to the end effectors.

8. The bipolar bioptome of claim 1, wherein the first conductive portion includes an electrically conductive control wire electrically coupled to the distal member.

9. The bipolar bioptome of claim 1, wherein the distal member includes a cylinder having a substantially non-conductive distal edge.

10. The bipolar bioptome of claim 1, wherein distal member includes a cylinder having a substantially non-conductive interior surface and an exterior surface having electrically conductive portions.

11. The bipolar bioptome of claim 1, wherein the distal member includes a substantially non-conductive distal portion for electrically isolating the distal member from the end effectors.

12. The bipolar bioptome of claim 1, wherein the end effectors include a pair of resilient arms each terminating in a jaw.

13. The bipolar bioptome of claim 1, wherein the electrical coupling includes a first electrical connector for supplying the one pole of the current source to the distal member and a second electrical connector for supplying the other pole of the current source to the end effectors.

14. The bipolar bioptome of claim 1, wherein the distal end effector assembly is adapted for use in retrieving multiple biopsy samples from a body without withdrawal of the bioptome from the body.

15. A bipolar bioptome comprising:

a proximal handle assembly including an actuator;

a distal end effector assembly including electrically conductive end effectors and an electrically conductive actuation member electrically isolated from the end effectors and movable relative to the end effectors;

an electrically conductive flexible member and an electrically conductive control member mechanically coupling the actuator to the end effector assembly such that actuation of the actuator causes the actuation member to move relative to the end effectors and thereby open and close the end effectors, wherein the flexible member and the control member are electrically isolated from each other, and wherein the flexible member is electrically coupled to one of the actuation member and the end effectors and the control member is electrically coupled to the remaining other of the actuation member and the end effectors; and an electrical coupling for supplying one pole of a current source to the flexible member and the other pole of the current source to the control member so that current flows between the actuation member and the end effectors during a biopsy procedure.

16. The bipolar bioptome of claim 15 wherein the electrically conductive flexible member is electrically coupled to the end effectors.

17. The bipolar bioptome of claim 15, further comprising a non-conductive sheath over at least a portion of the flexible member.

18. The bipolar bioptome of claim 15, wherein the flexible member is a coil.

19. The bipolar bioptome of claim 15, wherein the electrically conductive control member is electrically coupled to the end effectors.

20. The bipolar bioptome of claim 15, further comprising a non-conductive sheath over at least a portion of the control member.

21. The bipolar bioptome of claim 15, wherein the electrically conductive flexible member is electrically coupled to the actuation member.

22. The bipolar bioptome of claim 15, wherein the electrically conductive control member is electrically coupled to the actuation member.

23. The bipolar bioptome of claim 15, wherein the actuation member includes a cylinder having a substantially non-conductive distal edge.

24. The bipolar bioptome of claim 15, wherein the actuation member includes a cylinder having a substantially non-conductive interior surface and an exterior surface having electrically conductive portions.

25. The bipolar bioptome of claim 15, wherein the actuation member includes a substantially non-conductive distal portion for electrically isolating the actuation member from the end effectors.

26. The bipolar bioptome of claim 15, wherein the end effectors include a pair of resilient arms each terminating in a jaw.

27. The bipolar bioptome of claim 15, wherein the electrical coupling includes a first electrical connector for supplying the one pole of the current source to the flexible member and a second electrical connector for supplying the other pole of the current source to the control member.

28. The bipolar bioptome of claim 15, wherein the distal end effector assembly is adapted for use in retrieving multiple biopsy samples from a body without withdrawal of the bioptome from the body.

* * * * *